US012758737B2

(12) United States Patent
Tsoneva et al.

(10) Patent No.: US 12,758,737 B2
(45) Date of Patent: Oct. 13, 2026

(54) METHOD FOR ESTIMATING DEVICE FIT USING PHYSIOLOGICAL DATA

(71) Applicant: KONINKLIJKE PHILIPS N.V., Eindhoven (NL)

(72) Inventors: Tsvetomira Kirova Tsoneva, Eindhoven (NL); Daan Anton Van Den Ende, Breda (NL); Sander Theodoor Pastoor, Vleuten (NL); Stefan Pfundtner, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 970 days.

(21) Appl. No.: 18/082,991

(22) Filed: Dec. 16, 2022

(65) Prior Publication Data

US 2023/0211117 A1 Jul. 6, 2023

Related U.S. Application Data

(60) Provisional application No. 63/294,971, filed on Dec. 30, 2021.

(51) Int. Cl.
*A61M 21/00* (2006.01)

(52) U.S. Cl.
CPC ..... *A61M 21/00* (2013.01); *A61M 2021/0027* (2013.01); *A61M 2205/13* (2013.01);
(Continued)

(58) Field of Classification Search
CPC .......... A61M 21/00; A61M 2021/0027; A61M 2205/13; A61M 2205/3303;
(Continued)

(56) References Cited

U.S. PATENT DOCUMENTS

2011/0071416 A1 3/2011 Terada et al.
2016/0239084 A1 8/2016 Connor
(Continued)

OTHER PUBLICATIONS

Tononi et al., "Sleep function and synaptic homeostasis" Sleep Med. Reviews (2006) 10, pp. 49-62, Madison, WI.
Riedner et al., "Enhancing sleep slow waves with natural stimuli" Medicamundi. 45, 82-88, Jan. 2010, Madison, WI.
Regan et al., "Human brain electrophysiology: evoked potentials and evoked magnetic fields in science and medicine", Elsevier, vol. 12, No. 6, 1989.
(Continued)

*Primary Examiner* — Sunita Reddy
(74) *Attorney, Agent, or Firm* — Michael W. Haas

(57) ABSTRACT

Methods and systems are provided for assisting a user of a wearable biosignal monitoring device (2) in adjusting the device to achieve optimum fit and positioning. The biosignal monitoring devices considered use integrated bio sensors (5) to monitor the user's physiological activity for various purposes such as tracking daily activity patterns, determining mood, and monitoring sleep stages, among others. It is determined either during device setup or during primary use of the device whether the current fit and positioning of the device (2) enable the bio sensors (5) to properly sense the physiological signals needed for the device to perform its primary function. The user is then informed either after initial device setup whether adjustments need to be made in order to optimize device function during primary use, or is informed after primary use whether adjustments need to be made in order to improve device function during future primary use.

15 Claims, 7 Drawing Sheets

(52) U.S. Cl.
CPC ............... *A61M 2205/3303* (2013.01); *A61M 2205/502* (2013.01); *A61M 2205/702* (2013.01); *A61M 2230/10* (2013.01)

(58) Field of Classification Search
CPC ...... A61M 2205/502; A61M 2205/702; A61M 2021/0022; A61M 2021/0044; A61M 2205/3306; A61M 2205/3317; A61M 2205/3592; A61M 2205/505; A61M 2205/52; A61M 2205/581; A61M 2205/582; A61M 2205/584; A61M 2205/587; A61M 2205/70; A61M 2209/088; A61M 21/02; A61M 2230/10; A61M 2210/04; A61M 2230/04; A61M 2230/06; A61M 2230/42; A61M 2230/60; A61M 2230/63; A61M 2230/65
USPC ...................................................... 600/26–28
See application file for complete search history.

(56) References Cited

U.S. PATENT DOCUMENTS

| | | | | |
|---|---|---|---|---|
| 2017/0151436 | A1* | 6/2017 | Flaherty ............... | A61B 5/0531 |
| 2017/0259029 | A1* | 9/2017 | Dementienko ....... | A61M 21/02 |
| 2018/0333558 | A1* | 11/2018 | Levendowski ...... | A61B 5/4076 |
| 2019/0021665 | A1 | 1/2019 | Kesinger et al. | |
| 2019/0133488 | A1* | 5/2019 | Meftah .................. | A61B 5/349 |
| 2020/0008739 | A1* | 1/2020 | Qian .................... | A61B 5/6831 |
| 2020/0139112 | A1 | 5/2020 | Aharonovitch et al. | |
| 2020/0261689 | A1* | 8/2020 | Harrison .............. | A61B 5/6831 |
| 2023/0376114 | A1* | 11/2023 | Qian ...................... | A61B 5/389 |

OTHER PUBLICATIONS

Atienza et al., "Auditory information processing during human sleep as revealed by event-related brain potentials. Clinical Neurophysiology", TINS, vol. 12, pp. 2031-2045.

* cited by examiner

METHOD FOR ESTIMATING DEVICE FIT USING PHYSIOLOGICAL DATA

CROSS REFERENCE TO RELATED APPLICATION

This patent application claims the benefit of U.S. Application Ser. No. 63/294,971 filed Dec. 30, 2021, the contents of which are herein incorporated by reference.

BACKGROUND OF THE INVENTION

1. Field of the Invention

The disclosed concept pertains to biosignal monitoring devices used to detect various physiological states of the wearer, and, in particular, to methods and systems for improving the fit of such devices in an automated manner.

2. Description of the Related Art

Wearable biosignal monitoring devices are often used to provide valuable insight into a variety of conditions of the device user: daily activity patterns, mood, sleep stage, etc. These devices use physiological sensors to detect biosignals such as EEG, heart rate, $SpO_2$, etc. in order to provide such insight. Many wearable biosignal monitoring devices are available for at-home consumer use, including, for example and without limitation, wrist-worn smart watch devices, respiration belts, smart adhesive patches, finger sensors, and therapeutic sleep headbands. One such at-home biosignal monitoring device is the SmartSleep Deep Sleep Headband (DSH) manufactured and distributed by Philips. The DSH is a non-invasive portable head-worn device which uses biosignal monitoring to determine the sleep stage of the wearer and selectively deliver soft non-arousing tones through a speaker at appropriate stages of sleep in order to stimulate deep sleep, thereby reducing daytime sleepiness associated with insufficient sleep or poor perceived sleep quality. Research shows that peripheral stimulation (e.g. electric, magnetic, or sensory) during deep sleep can improve slow-wave activity and increase the restorative value of sleep. The DSH delivers stimulation to a user in a closed loop manner by: monitoring the user's electroencephalogram (EEG) during sleep, identifying appropriate moments for stimulation, and delivering auditory stimulation to improve sleep slow waves without causing arousals. The DSH monitors EEG though electrodes integrated in the headband and delivers therapy via a bone conduction speaker or over a set of ear speakers also integrated in the headband.

The efficacy of wearable biosignal monitoring devices depends on the device being properly fit and and the sensors being properly positioned on the user so that the physiological activity of the user can be measured accurately. A consumer who uses a wearable biosignal monitoring device at home may not realize when a sensor is unable to accurately sense a physiological signal or how to properly adjust the fit of the monitoring device in order to fix the positioning of the sensor for optimal signal detection. If the device is too loose, the signal quality of the bio sensor will likely be poor due to bad detection of the desired physiological signal. Conversely, if the device is too tight, user comfort will be affected and may lead to non-compliance. For example, with respect to the DSH, if the device is too loose, the signal quality will be affected leading to poor detection of sleep stages and reduced therapy or no therapy delivery whatsoever. Conversely, if the device is too tight, user comfort will be affected leading to disturbed sleep, reports of pressure points, and headache.

Accordingly, there is room for improvement in methods and systems for adjusting the positioning of sensors included in wearable biosignal monitoring devices and for adjusting the fit of such devices.

SUMMARY OF THE INVENTION

Accordingly, it is an object of the present invention to provide, in an exemplary embodiment, a fit and positioning optimization system for a biosignal monitoring device that is configured to monitor the physiological signals of a user. The optimization system includes: a number of bio sensors configured to sense physiological activity of the user; a device fit event detector, the fit event detector comprising at least one of: a number of sensory event actuators configured to deliver sensory stimuli to the user, or a biosignal event detection unit comprising instructions for executing a number of event detection algorithms; a controller comprising a signal analysis unit and configured to be in electrical communication with the number of bio sensors and the fit event detector; and a user interface configured to be in electrical communication with the controller. The controller is configured to use the fit event detector to define a user response based on physiological activity signals sensed by the bio sensors. The signal analysis unit is configured to store physiological response reference data, and to determine if the user response is within a predefined normative range based on the reference data. The controller is configured to form a recommendation, based on whether the user response is within the normative range, indicating whether adjustments to the fit or positioning of the device are required in order to optimize monitoring of biosignals. The controller is also configured to then alert the user of the recommendation through the user interface.

In another embodiment, a method for optimizing fit and positioning for a biosignal monitoring device comprises first positioning the device on the user, said device being configured to monitor physiological activity of a user. The device includes a number of bio sensors, a fit event detector, a controller comprising a signal analysis unit, and a user interface configured to be in electrical communication with the controller. The fit event detector comprises at least one of: a number of sensory event actuators configured to deliver sensory stimuli to the user, or a biosignal event detection unit comprising instructions for executing a number of event detection algorithms. The signal analysis unit stores physiological response reference data and is configured to be in electrical communication with the number of bio sensors and the fit detector. The method further comprises: sensing physiological activity with the number of the bio sensors; defining, using the fit event detector, a user response based on the sensed physiological activity; determining, with the signal analysis unit, if the defined user response is within a predefined normative range based on the reference data; forming a recommendation, with the signal analysis unit, indicating whether the fit and/or positioning of the device require adjustments in order to optimize monitoring of physiological activity, based on whether the defined user response is within the normative range; and alerting the user of the recommendation through the user interface.

In a further embodiment, a method for optimizing fit and positioning for a wearable sleep therapy device comprises positioning the device on the user and performing a number of fit analyses after the device has been positioned on the user, the sleep therapy device being configured to monitor sleep stages of a user and deliver non-arousing auditory tones to the user to enhance sleep quality in response to the monitoring of the sleep stages. The device comprises: a number of EEG sensors; a number of speakers configured to selectively deliver sleep-improving auditory tones to the user during sleep; a fit event detector comprising at least one of a number of sensory event actuators comprising the number of speakers or a biosignal event detection unit comprising instructions for executing a number of event detection algorithms; a controller comprising a signal analysis unit configured to be in electrical communication with the number of EEG sensors, the signal analysis unit being configured to store physiological reference data; and a user interface configured to be in electrical communication with the controller. Performing the number of fit analyses comprises: sensing physiological activity of the user with the number of EEG sensors; defining, using the fit event detector, a user response based on physiological activity sensed by the number of EEG sensors; determining, with the signal analysis unit, if the physiological activity is within a predefined normative range based on the reference data; forming a recommendation, with the signal analysis unit, indicating whether the fit of the device requires adjustments in order to properly position either the EEG sensors or the speakers for monitoring of sleep stages or delivery of the non-arousing auditory tones, based on whether the fit-detecting physiological activity is within the normative range; and alerting the user of the recommendation through the user interface. The number of fit analyses can be performed either during wakefulness prior to sleep onset or after sleep onset, and the monitoring of the sleep stages is based on physiological signals sensed by the number of EEG sensors.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF EXEMPLARY EMBODIMENTS

Figure 1A:
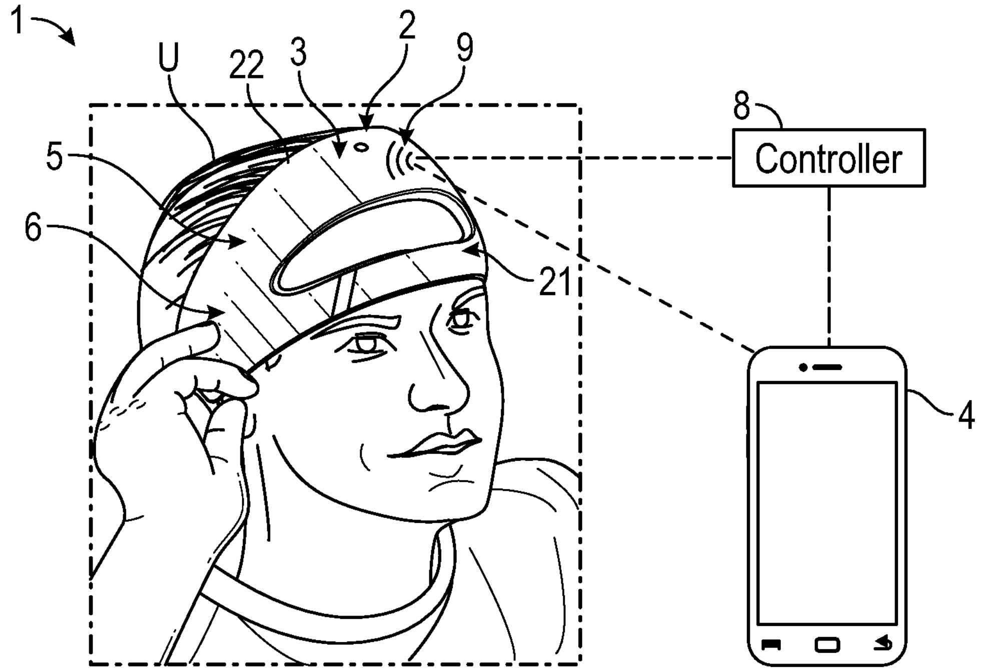
FIG. 1A shows a biosignal monitoring system with fit optimization guidance capability, including a sleep headband biomonitoring device and various schematically depicted electronic components, according to an exemplary embodiment of the disclosed concept.

As used herein, the singular form of "a", "an", and "the" include plural references unless the context clearly dictates otherwise.

The terms "bio signal" and "physiological signal" are used interchangeably herein.

As used herein, the statement that two or more parts or components are "coupled" shall mean that the parts are joined or operate together either directly or indirectly, i.e., through one or more intermediate parts or components, so long as a link occurs. The statement that two or more parts or components are "removably coupled" shall mean that the individual components are structured to be coupled to one another and can be decoupled from one another without comprising the structural integrity of either individual component.

As used herein, the term "number" shall mean one or an integer greater than one (i.e., a plurality).

As used herein, the term "controller" shall mean a number of programmable analog and/or digital devices (including an associated memory part or portion) that can store, retrieve, execute and process data (e.g., software routines and/or information used by such routines), including, without limitation, a field programmable gate array (FPGA), a complex programmable logic device (CPLD), a programmable system on a chip (PSOC), an application specific integrated circuit (ASIC), a microprocessor, a microcontroller, a programmable logic controller, or any other suitable processing device or apparatus. The memory portion can be any one or more of a variety of types of internal and/or external storage media such as, without limitation, RAM, ROM, EPROM(s), EEPROM(s), FLASH, and the like that provide a storage register, i.e., a non-transitory machine readable medium, for data and program code storage such as in the fashion of an internal storage area of a computer, and can be volatile memory or nonvolatile memory.

As used herein, the term "machine learning model" shall mean a software system that develops and builds a mathematical model based on sample data, known as "training data", in order to make predictions or decisions without being explicitly programmed to do so, including, without limitation, a computer software system that develops that has been trained to recognize patterns from a set of training data, and subsequently develops algorithms to recognize patterns from the training data set in other data sets.

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

The disclosed concept, as described in greater detail herein in connection with various particular exemplary embodiments, provides automated methods and systems for assisting a user of a wearable biosignal monitoring device (also referred to herein as a "biomonitoring device") in adjusting the device to ensure that the device is properly fit and that the bio sensors of the device are properly positioned after the user has put the device on. Biosignal monitoring devices generally utilize sensors such as electrodes to detect physiological signal activity, and it will be appreciated that good skin contact and low electrode impedance are essential for optimizing the signal quality of physiological activity detected by electrodes. Research and medical grade systems for measuring physiological activity usually require a preparation step consisting of skin cleaning, electrode set up, and conductive gel application in order to ensure good skin contact and low electrode impedance. With respect to consumer grade systems intended for at-home use though, such elaborate and time-consuming set up procedures are usually undesirable from a user perspective. However, proper device placement and good fit are just as important for ensuring the quality of the measured signal, therapy delivery (where applicable), and user satisfaction in consumer grade applications as they are in research and medical grade applications. Thus, the methods and systems of the present invention facilitate effective measurement of physiological signals in consumer grade wearable biosignal monitoring devices by determining during device setup if the device is properly fit and if the sensors are properly positioned, and, upon detection of improper fit and/or positioning, guiding the user in adjusting the positioning and/or fit of the device as appropriate.

Referring now to FIG. 1A, an example embodiment of a wearable biosignal monitoring system 1 comprising a biomonitoring device 2, specifically a therapeutic sleep headband 2 (shown disposed on the head of a user U), a signal analysis unit 3 (integrated within Sleep headband 2 and not visible in the figure), and a user interface 4 is shown. Sleep headband 2 is configured to selectively deliver therapeutic tones through a speaker at appropriate stages of sleep in order to stimulate deep sleep. Signal analysis unit 3 is described later herein with respect to FIG. 2, and a machine learning model 30 that can optionally be included in signal analysis unit 3 is described later herein with respect to step 103 of method 100 depicted in FIG. 4. User interface 4 can comprise, for example and without limitation, any personal computing device such as a mobile phone or tablet, or it can be a component integrated into the wearable biomonitoring device 2 itself. Sleep headband 2 comprises a number of bio sensors 5 integrated within headband 2 (bio sensors 5 not being visible in FIG. 1A), and can optionally comprise a number of sensory actuators 6, which are structured to provide a number of different types of stimulation, as detailed later herein.

Figure 1B:
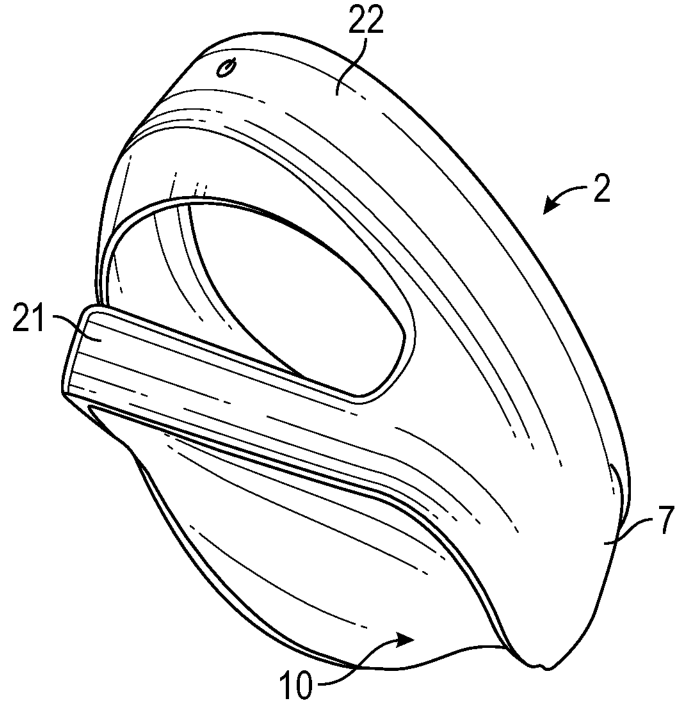
FIG. 1B shows a perspective view of the sleep headband biomonitoring device shown in FIG. 1A.

For the sake of brevity, because wearable biosignal monitoring devices are available in several different forms (wrist-worn devices, respiration belts, smart adhesive patches, finger sensors, etc.), the methods of the present invention are discussed herein primarily using the sleep headband 2 pictured in FIGS. 1A and 1B as an illustrative example. It should be noted that discussion of the sleep headband 2 is intended to provide clarity regarding how the inventive concepts disclosed herein can be implemented in a physical device, and is not intended to exclude application of said concepts to biosignal monitoring devices other than a sleep headband. Accordingly, reference may be made herein to either a "biomonitoring device" 2 (i.e. a generic biosignal monitoring device) or a "sleep headband" 2, and it should be understood that statements made regarding biomonitoring device 2 are applicable to sleep headband 2 and that statements made regarding sleep headband 2 are applicable to biomonitoring device 2, unless specifically stated otherwise. In general, the term "sleep headband" is used herein specifically when context necessitates referring to the specific physical structure of a therapeutic sleep headband, e.g. by virtue of the sleep headband being a head worn device rather than a non-head worn device; otherwise, the term "biomonitoring device" is used.

Continuing to refer to FIG. 1A, while all of the biomonitoring devices 2 considered herein are assumed to include bio sensors 5, it should be noted that not all types of biomonitoring devices 2 include sensory actuators 6, although many do. As shown in FIG. 1B, sleep headband 2 further comprises an ear region 7 that is structured to be positioned over the ear of user U, as well as a forehead band 21 structured to be disposed on the forehead of user U and a scalp band 22 structured to be disposed on the scalp of user U.

In an exemplary embodiment of sleep headband 2, bio sensors 5 comprise EEG sensors integrated into either or both of the forehead band 21 and scalp band 22. Sensory actuators 6 can comprise, for example and without limitation, auditory, visual, and/or tactile stimulators. In exemplary embodiments of sleep headband 2, sensory actuators 6 comprise at least auditory stimulators such as speakers, in order to perform the primary device function of delivering therapeutic tones during deep sleep for the purpose of enhancing slow-wave brain activity. However, it should be noted that such auditory sensory actuators 6 can provide stimulation during wakefulness as part of the disclosed guided device setup, detailed further herein with respect to Method 100 depicted in FIG. 5.

Said auditory sensory actuators 6 of sleep headband 2 may comprise, for example and without limitation, a bone conduction speaker integrated into the forehead band 21 or ear speakers integrated into the ear region 7. Sensory actuators 6 of sleep headband 2 may also additionally comprise visual and/or tactile stimulators, the uses of which are also detailed further later herein with respect to FIG. 5. Visual stimulation may be provided, for example and without limitation, on a screen of user interface 4 or via LEDs integrated into the sleep headband 2 itself, and said tactile stimulation may be provided, for example and without limitation, by configuring user interface 4 or the sleep headband 2 itself to produce haptic stimulation. It will be appreciated that the specific examples of auditory, visual, and tactile stimulation described with respect to sleep headband 2 are also applicable to many other types of biomonitoring devices 2.

As schematically depicted in FIG. 1A, biosignal monitoring system 1 additionally comprises a controller 8 and a communication module 9. Controller 8 has software execution, data processing, and data storage capabilities. Communication module 9 is configured to facilitate either direct or indirect wireless communication between signal analysis unit 3, controller 8, and user interface 4, and may comprise, for example and without limitation, Wi-Fi or Bluetooth communication capability. Although FIG. 1A depicts controller 8 and biomonitoring device 2 as discrete components such that controller 8 is external to biomonitoring device 2, it should be noted that this depiction is for illustrative purposes in order to denote the presence of controller 8 and is not intended to be limiting on the actual physical setup of controller 8 relative to biomonitoring device 2.

In an exemplary embodiment, controller 8 is integrated within biomonitoring device 2 and comprises both signal analysis unit 3 and communication module 9. Accordingly, in FIG. 1A, the dashed line depiction of communication between wireless module 9, controller 8, and user interface 4 is intended to be a non-limiting representation of how data can be transmitted between user interface 4 and signal analysis unit 3 and/or controller 8. User interface 4 enables communication between user U, signal analysis unit 3, and controller 8 in order to, for example and without limitation, display the analysis of the device 2 fit and positioning performed by signal analysis unit 3 or allow user U to initiate guided user setup as detailed herein with respect to method 100 depicted in FIG. 5.

As indicated in FIG. 1B, sleep headband 2 comprises a fit adjuster 10 (not visible in the figures) structured to be disposed against the rear side of the head when sleep headband 2 is worn by user U. Fit adjuster 10 can comprise any adjustment mechanism suitable for adjusting the size and positioning of sleep headband 2, such as, for example and without limitation, a slide adjustment mechanism or a hook and loop fastener. It will be appreciated that fit adjustment mechanisms serving a purpose functionally equivalent to fit adjuster 10 are ubiquitous in biosignal monitoring devices, and that said fit adjustment mechanisms enable a wearable biomonitoring device 2 to be adjusted in order to enable the bio sensors 5 to properly measure the intended physiological signals of the user. Fit adjustment is detailed further later herein with respect to step 104 of method 100 depicted in FIG. 4.

Figure 2:
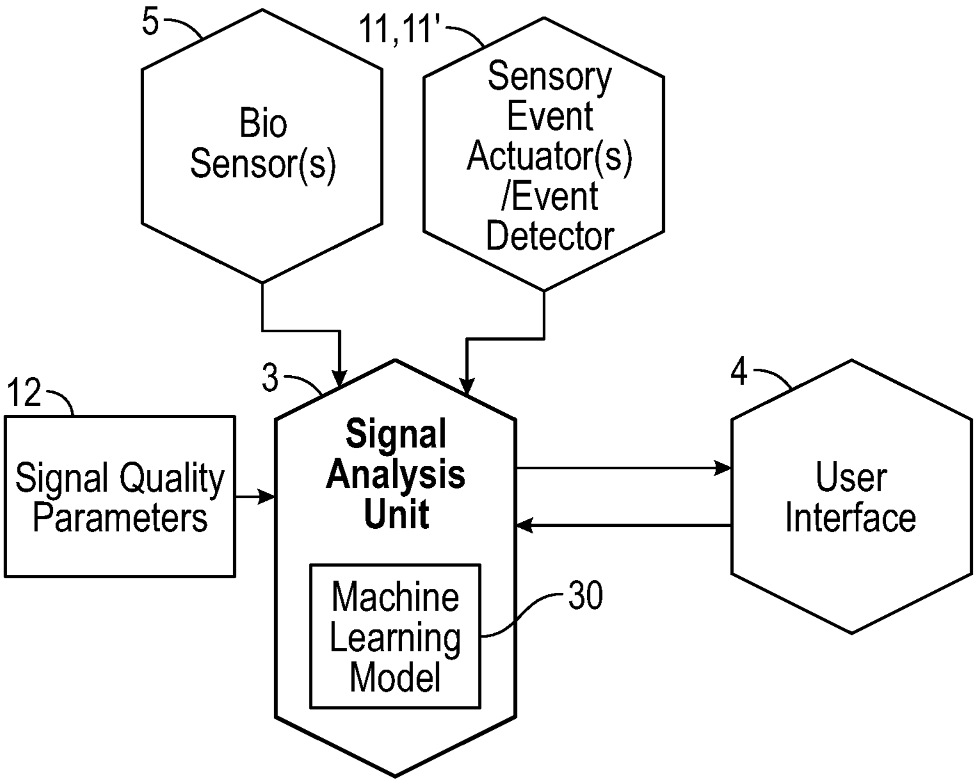
FIG. 2 is a schematic diagram depicting the communication between various electronic components of the biosignal monitoring system shown in FIG. 1A, according to an exemplary embodiment of the disclosed concept.

Referring now to FIG. 2, a schematic depiction of the communication between various electronic components of biosignal monitoring system 1 is shown. Controller 8 either comprises or is in communication with all of the electronic components depicted in FIG. 2. As shown in FIG. 2, biomonitoring device 2 comprises a fit event detector 11, 11', either a biosignal event detection unit 11 (also referred to herein as a bio event detector 11) or a sensory event actuator 11', that provides input to signal analysis unit 3 for the purpose of performing a device fit analysis. When user U is wearing biomonitoring device 2, signal analysis unit 3 uses fit event detector 11,11' to compare the signals sensed by bio sensors 5 to stored typical signal values in order to determine whether the positioning of bio sensors 5, and consequently, the fit of device 2, are satisfactory for proper device 2 functioning.

The distinction between bio event detector 11 and sensory event actuator 11' arises from the type of event that each detects. Bio event detector 11 detects spontaneous physiological signals in user U. In contrast, sensory event actuator 11' generates and delivers stimuli to user U via sensory actuators 6 for the purpose of eliciting a physiological response in user U, and subsequently transmits information about the timing of the stimuli delivery to signal analysis unit 3. Both bio event detector 11 and sensory event actuator 11' are detailed further herein below. It should be further noted that monitoring system 1 comprises bio event detector 11 in some exemplary embodiments, and alternatively comprises sensory event actuator 11' in other exemplary embodiments. Monitoring system 1 can, however, comprise both a bio event detector 11 and sensory event actuator 11' without departing from the scope of the disclosed concept.

Bio event detector 11 receives input from bio sensors 5 and is configured to execute a number of event detection algorithms in order to detect spontaneous physiological events expected to be present in biosignals typically obtained from the location in which a given bio sensor 5 is positioned. Said spontaneous physiological events can include commonly detected signal artefacts. Event detection algorithms can be used to detect many different types of spontaneous physiological signals, including eye blinks, heart rate, muscle movement, etc. In one non-limiting illustrative example, eye blinks are artefacts commonly detected in EEG signals, particularly scalp EEG signals, and bio event detector 11 can be configured to detect eye blink signal artefact data from a scalp EEG signal. It is expected that scalp EEG sensors integrated into a biomonitoring device 2, such as scalp EEG electrode bio sensors 5 that can be integrated into scalp band 22 of sleep headband 2, would produce EEG signals with well-defined eye blink artefact data.

Figure 4:
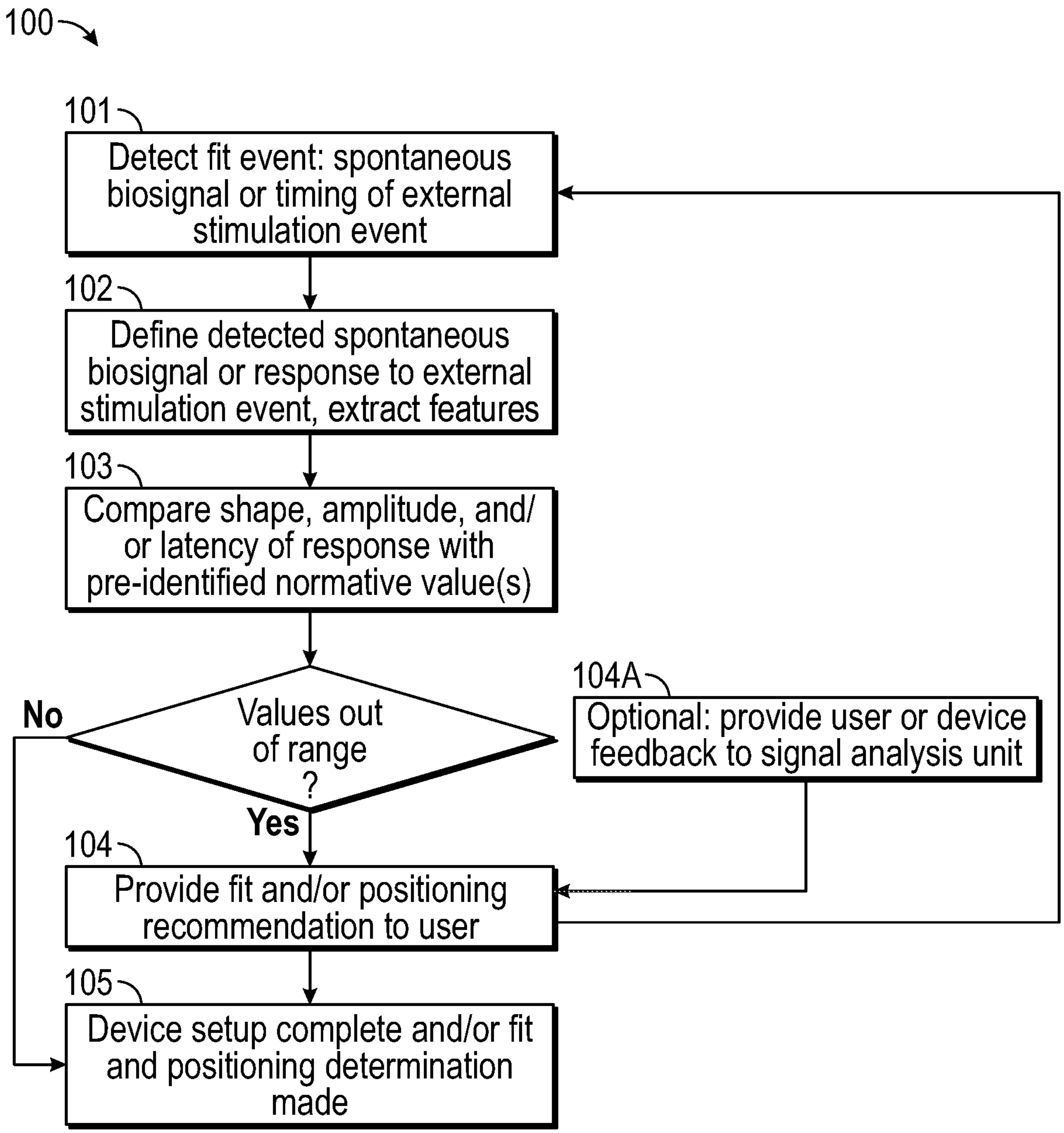
FIG. 4 is a flow chart depicting the steps of a method to be executed by the biosignal monitoring system shown in FIG. 1A in order to determine whether the biomonitoring device has been properly fit and positioned for wear by the user, according to an exemplary embodiment of the disclosed concept.

Bio event detector 11 transmits each detected spontaneous event signal as input to signal analysis unit 3, and signal analysis unit 3 then compares the spontaneous event signal to normative signal data considered typical for the particular event type detected in order to determine if the signal sensed by bio sensor 5 is of satisfactory quality, as detailed further herein with respect to method 100 depicted in FIG. 4. It will be appreciated that several stereotypical spontaneous physiological responses other than eye blinks are also very well studied and documented in scientific literature, and it should be understood that a bio event detector 11 for a particular biomonitoring system 1 can be configured to detect whichever stereotypical spontaneous physiological responses are appropriate for the context in which the particular biomonitoring system 1 is used. These other stereotypical responses include responses generated by the brain (including event related potentials, "ERPs", detailed later herein), responses generated by the autonomous nervous system, muscle activity, sweat glands, respiration, eye movement, finger tapping, (imagined) finger/limb movement, EEG power ratio of eyes closed to eyes open, heart rate, heart rate variability, galvanic skin response, respiration rate, among many others.

Figure 3A:
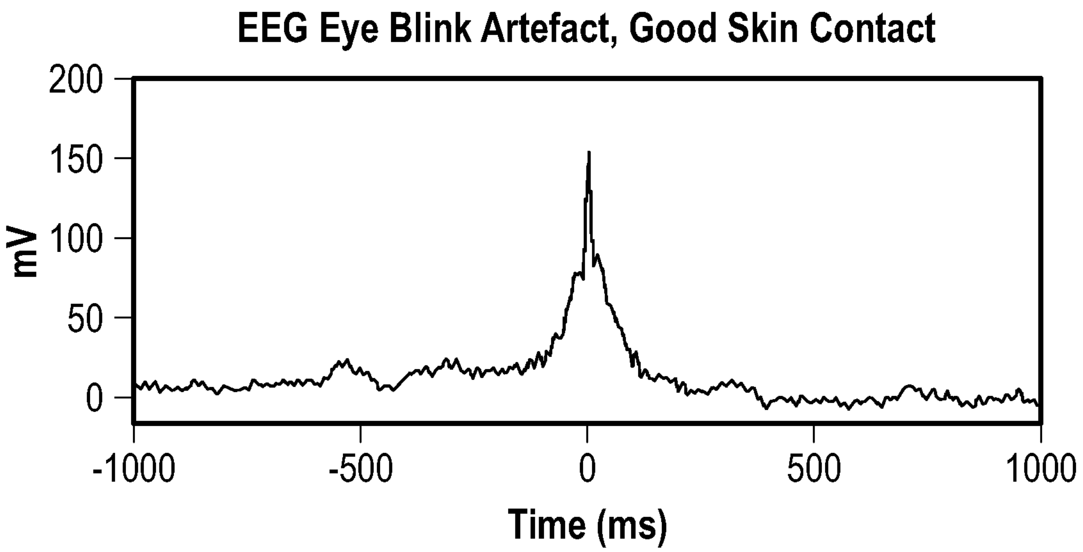
FIG. 3A is a graph of eye blink artefact in an EEG signal indicative of good contact between the skin of a device user and an EEG electrode of the biomonitoring device shown in FIG. 1A, representative of reference data used by the biosignal monitoring system to determine whether device fit and positioning is satisfactory, according to an exemplary embodiment of the disclosed concept.
Figure 3B:
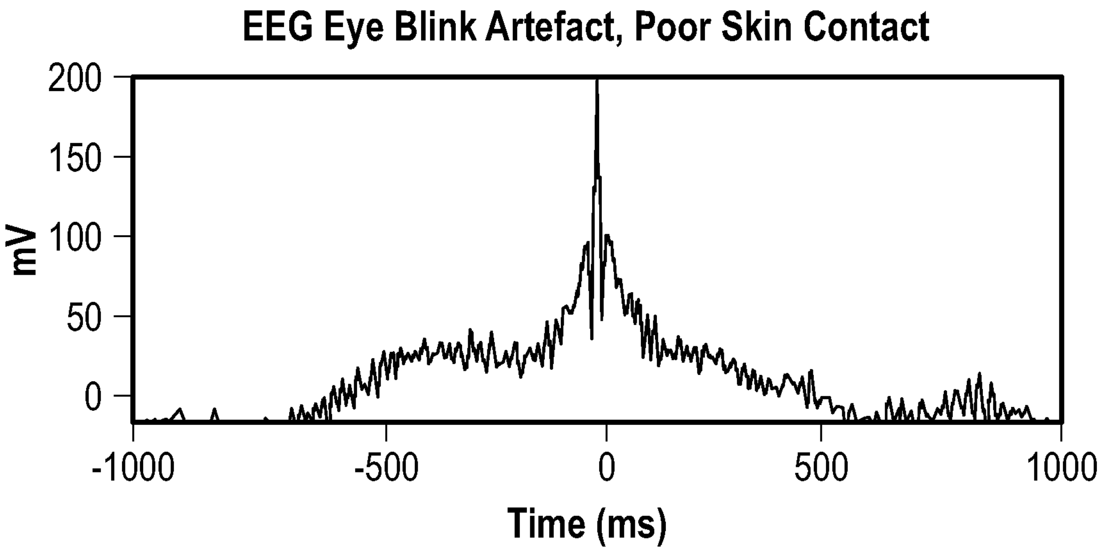
FIG. 3B is a graph of eye blink artefact in an EEG signal indicative of poor contact between the skin of a device user and an EEG electrode of the biosignal monitoring system shown in FIG. 1A, representative of reference data used by the biosignal monitoring system to determine whether device fit and positioning is satisfactory, according to an exemplary embodiment of the disclosed concept.

Still referring to bio event detector 11, in FIG. 3A, eye blink artefact data from an EEG signal sensed by an EEG electrode bio sensor 5 with good skin contact and positioning is shown. In FIG. 3B, eye blink artefact data from an EEG signal sensed by an EEG electrode with poor skin contact and positioning is shown. For a biomonitoring device 2 in which an EEG bio sensor 5 would be expected to detect eye blink signal data, signal analysis unit 3 is programmed and configured such that, if signal analysis unit received eye blink signal data such as that shown in FIG. 3A, i.e. with very little to no noise, signal analysis unit 3 would recognize that the signal has very little to no noise based on feature extraction performed in accordance with a feature extraction process 120 detailed further herein with respect to FIG. 5, determine that the skin contact between the bio sensor 5 and skin of user U is good, and determine that the fit of device 2 is good. In contrast, if signal analysis unit 3 received eye blink signal data such as that shown in FIG. 3B, signal analysis unit 3 would recognize that the eye blink signal is very noisy based on feature extraction, determine that the electrode producing the signal has poor skin contact, and determine that the device 2 is too loose. While the signal in FIG. 3B is noisy and indicates somewhat poor sensor to skin contact, the presence of a discernible signal indicates that there is at least some contact between the bio sensor 5 and the skin of user U, and it will be appreciated that in the case of there being very poor to no contact between the skin of user U and a sensor 5, a well-defined signal would be altogether lacking.

Referring again to FIG. 2, in contrast to detecting spontaneous physiological events as bio event detector 11 does, sensory event actuator 11' actuates a sensory actuator 6 to deliver an externally generated physiological stimulus to user U and transmits information about the timing of the delivered stimulus as input to signal analysis unit 3. Signal analysis unit 3 then determines the trigger time of the physiological signal(s) produced in user U in response to the stimulus event(s) actuated by sensory event actuator 11' and analyzes the response signal quality. For example, user interface 4 of sleep headband 2 can comprise a mobile phone with a dedicated sleep headband user platform app, and said user platform app can be used to provide stimulation to user U as part of a guided device setup that user U can initiate after donning sleep headband 2.

Continuing with the same example, the mobile phone user platform app can be used to trigger a stimulus to be provided by the sensory actuator(s) 6 integrated within the headband 2. For example, the app can actuate an LED integrated within headband 2 to produce flashing light. Another non-limiting example in a different biomonitoring device 2 is using the app to produce a vibration in a wrist-worn device. Alternatively, the mobile phone itself can produce the stimulation, for example and without limitation by producing a light flash on the phone screen for visual stimulation, or by producing a vibration through the phone for haptic stimulation. It will be appreciated that in this case, the mobile phone comprises not only user interface 4, but sensory event actuator 11' and sensory actuator 6 as well. Even though visual and haptic stimulation are not part of the therapy delivered by the sleep headband 2 when user U is sleeping, the responses of user U to the visual or haptic stimulation sensed by the bio sensors 5 can still be compared to normative data stored in signal analysis unit 3 to determine if bio sensors 5 have sufficient contact and are well-positioned. While the delivered stimulation does not have to be related to the primary function of biomonitoring device 2 in order to produce a useful fit analysis, sensory event actuator 11' can be especially useful if one of the primary functions of device 2 is to deliver a particular type of stimulus. In one non-limiting example, in the case of sleep headband 2, sensory event actuator 11' can cause an auditory sensory actuator 6 to play a number of auditory tones in order to determine during wakefulness whether user U will respond meaningfully during sleep to delivery of therapeutic tones based on the current device fit and positioning.

In an exemplary embodiment, one specific type of user response that signal analysis unit 3 defines is an event related potential (ERP). Both external and internal events are known to elicit stereotypical brain responses, with each response comprising a time and phase locked to event onset. Such time- and phase-locked event responses are ERPs. Specifically, ERPs are voltage fluctuations arising from summed postsynaptic potentials of large neural populations firing synchronously during processing of information. ERPs are calculated as the average waveform over a number of events, and the amplitude and latency of the successive peaks in the ERP waveform can be used to determine the time course of information processing in the brain. Stimulation of increasing intensity (volume, in the case of auditory stimulation) produces reliable increase in the ERP amplitude. Biomonitoring devices 2 whose bio sensors 5 include scalp EEG sensors (including, for example and without limitation, sleep headband 2) are particularly good candidates for using a sensory event actuator 11' to determine ERP, as the high time resolution of scalp recorded EEG generally provides a good basis for studying the brain responses to external or internal events.

Both the spontaneous physiological events detected by bio event detector 11 and the user response to external stimulus events actuated by sensory event actuator 11' constitute "fit events". It should be noted that evaluation of fit events detected by fit event detectors 11,11' is an advantageous feature of the present invention, as the fit event evaluation performed by signal analysis unit 3 ensures that meaningful physiological responses that are expected to occur in the body when biomonitoring device 2 is being used for its primary purpose are detectable from the same types of physiological signals detected during device setup, prior to using the device for its primary use. For example and without limitation, the primary purpose of sleep headband 2 is to detect sleep stages of user U by monitoring the EEG bio sensor 5 signals with controller 8, and to deliver soft non-arousing tones to user U during deep sleep in order to enhance slow-wave brain activity. When performing device setup during wakefulness, the same EEG bio sensors 5 that controller 8 uses to detect sleep stages are also used to detect fit events with fit event detector 11,11' (e.g. to detect eye blink artefact in the EEG signals in the case of event detector 11, or determine ERPs in the case of sensory event actuator 11' actuating sensory actuators 6 to deliver external stimulation). Determining that eye blink signal artefact or ERPs are within a normative range during wakefulness increases the likelihood that EEG bio sensors 5 will properly determine the sleep stage of user U during sleep and that the delivered therapeutic auditory tones will be effective in enhancing slow-wave activity during deep sleep.

In additional exemplary embodiments, controller 8 may optionally comprise a signal quality parameter module 12, configured to determine various additional attributes of the signals detected by bio event detector 11 or elicited by sensory event actuator 11' and provide those attributes as additional inputs to signal analysis unit 3 in order to further refine the analysis of whether the positioning of bio sensors 5 is satisfactory. Such signal attributes can include, for example and without limitation, impedance, signal power, noise, and signal-to-noise ratio (SNR).

Referring now to FIG. 4, a flow chart is shown depicting the steps of a method 100 for determining whether the fit and positioning of biomonitoring device 2 on user U are optimized for the biosignal monitoring used for the primary device purpose. The method of FIG. 4 may be employed, for example, with a biosignal monitoring system such as biosignal monitoring system 1 shown in FIG. 1. However, it will be appreciated that the method may be employed with other biosignal monitoring systems as well without departing from the scope of the disclosed concept. It should be noted that both the fit and the positioning of biosignal monitoring device 2 need to be correct in order to ensure that the device can properly measure physiological signals produced by user U. Specifically, regarding device fit, bio sensors 5 must have sufficient contact with user U to get an accurate physiological signal reading. Regarding device positioning, the signals being measured by the bio sensors 5 must actually be the intended signals, and sources of artifacts or signal interference should be minimized. For example, when using sleep headband 2, bio sensors 5 should not be positioned over hair, the temples, certain muscles, or arteries, as these regions (as well as others) produce signals of poor quality. In one non-limiting example of poor fit, if a biosignal monitoring device 2 is too loose and one of the dry electrode bio sensors 5 is only just touching the skin, the signal measured by the bio sensor 5 will have a very low noise level but the dynamic range of the signal will be low due to the lack of pressure.

At step 101 of method 100, after user U has put on biomonitoring device 2, controller 8 detects a fit event using fit event detector 11,11' as previously detailed with respect to FIG. 2. If monitoring system 1 includes a bio event detector 11, then the fit event comprises the spontaneous biosignal(s) sensed by bio sensors 5 after the device 2 is donned by user U. If monitoring system 1 includes a signal actuator 11' instead, then the fit event is the timing of the external stimulation event, i.e. the timing of the physiological stimulation delivered to user U. It should be noted that fit events can be detected both during setup of a biomonitoring device 2 and during the primary use of the biomonitoring device 2, to account for the scenario in which the device 2 is deemed to be properly set up before the primary use of the device 2 begins but then worsens during the primary use of the device. It will be appreciated that fit events can be detected during device setup and during device primary use whether monitoring system 1 includes a bio event detector 11 or a sensory event actuator 11'. For example and without limitation, in the context of sleep headband 2, a bio event detector 11 can detect eye blinks in wakefulness and heart beats during sleep, while a signal actuator 11' can cause a user response to a light flash in wakefulness and a user response to auditory tones during sleep.

Still referring to step 101 in the context of sleep headband 2, detecting fit events during both wakefulness and sleep provides useful information in a scenario where user U sets up sleep headband 2 properly but the device 2 shifts in the night for some reason and consequently shifts the bone conduction speaker sensory actuator 6. In some exemplary embodiments, detection of fit events during wakefulness is omitted altogether and fit feedback is only provided after the sleep session based on the sensed responses of user U to the therapeutic auditory tones delivered during sleep. In a scenario where fit feedback is provided to user U based on responses to therapeutic tones delivered during sleep, regardless of whether or not fit feedback was also provided to user U during wakefulness, after user U wakes up, the monitoring system 1 can provide recommendations via user interface 4 for correcting the fit and/or positioning of sleep headband 2 in order to avoid the recurrence of adverse fit or positioning issues in the future. For example and without limitation, the user interface 4 can be configured to explain to user U that the bone conduction speaker was not properly positioned or connected, and provide tailored advice for avoiding recurrence of the issue in the future.

At step 102, a user response based on either the spontaneous physiological signal detected at step 101 (when monitoring system 1 includes bio event detector 11) or the response of user U to the stimuli delivered at step 101 (when monitoring system 1 includes signal actuator 11') is defined. Specifically, signal analysis unit 3 quantifies various features of the measurements taken by bio sensors 5 during the fit event detection at step 101. As previously stated, in the exemplary embodiment wherein monitoring system 1 includes bio event detector 11, signal analysis unit 3 uses a response event detection algorithm, (e.g. blink detector, heart rate detector, muscle movement detector, etc.), to detect the presence of a corresponding specific physiological signal. In the exemplary embodiment wherein monitoring system 1 includes sensory event actuator 11', signal analysis unit 3 does not need to include an event detection algorithm, as information regarding the timing of the stimuli is provided directly to signal analysis unit 3 by the sensory event actuator 11'. In either embodiment, i.e. whether monitoring system includes bio event detector 11 or sensory event actuator 11', the physiological response locked to the fit event timing (the fit event being the spontaneously occurring physiological signal in user U or the specific external stimulation event determined to have elicited a specific physiological signal in user U) is analyzed either as a response to a single event or as an average response over multiple events. It should be noted that if no event is detected where one was expected (e.g. eye blinks before sleep onset while wearing a sleep headband 2, an ERP produced in response to a sensory stimuli), the lack of response is considered an indication of device fit/signal quality issues.

Still referring to step 102, it should be noted that, generally, measuring responses over a period of time, and measuring multiple types of spontaneous physiological signals (when bio event detector 11 is used) or measuring responses to multiple types of stimuli (when sensory event actuator 11' is used), will produce a better estimation of device fit/positioning, in comparison to measuring a response for a single event or measuring a response to a single stimulus. Accordingly, in an exemplary embodiment, the user response can be defined as the average response over all stimulation events, which can be calculated as the average waveform in a window of predefined duration around event onset. For example and without limitation, in the context of an auditory stimulus, the time of tone onset is identified, and a cutoff time of 1 second before and 1 second after tone onset is implemented in order to define a 2-second window of time centered on event onset (i.e. tone onset) in order to identify the physiological response of user U during that 2-second window of time. Continuing with the same example, if 1,500 tones are played, then 1,500 2-second long physiological response waveforms are averaged to produce one 2-second long average response waveform, and the average response waveform constitutes the defined user response. After the user response is defined, relevant features are extracted. The features can include, for example and without limitation: the amplitude of first/second/etc. positive or negative peaks in the waveform; peak to peak distance; average amplitude or area under the curve in a predefined intervals; and others. To enhance signal to noise ratio, various filtering or fitting procedures can be applied before extracting the features. Additionally, single trial waveforms containing extreme values can be identified as containing artifacts and omitted prior to calculating the averaged response using absolute or relative thresholds (e.g. extreme values such as waveforms with an amplitude above 200 μV, or an amplitude exceeding the mean EEG amplitude by, e.g. 2 standard deviations, or an amplitude exceeding the $98^{th}$ percentile of all values).

Figure 5:
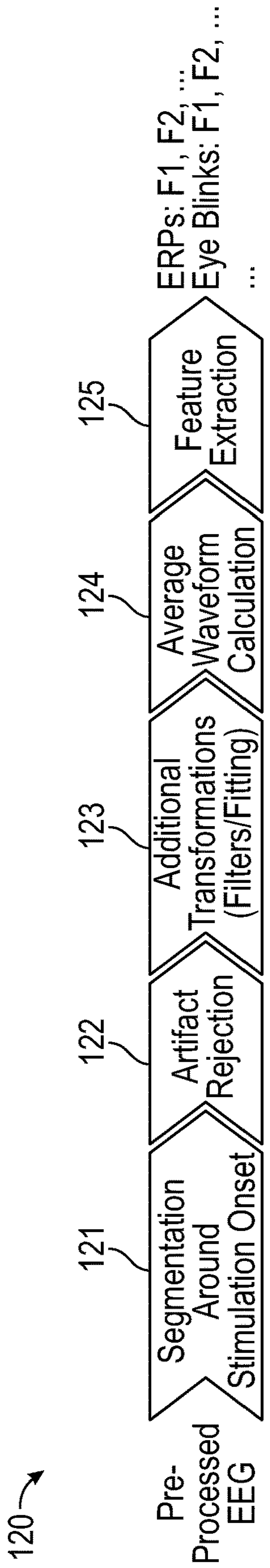
FIG. 5 is a flow chart depicting a feature extraction process used during a feature extraction step of the method depicted in FIG. 4, according to an exemplary embodiment of the disclosed concept.

Continuing to refer to step 102, the processing and quantification of either the spontaneous biosignal detected in user U or the response of user U to the stimuli delivered at step 101 is implemented in a feature extraction process 120 depicted in FIG. 5. It should be noted that although the feature extraction process 120 uses the illustrative example of an EEG signal in FIG. 5, the steps of FIG. 5 can easily be adapted to extract features of other types of signals such as EKG, EMG, and several others without departing from the scope of the disclosed concept. As shown in FIG. 5, at step 121, a pre-processed EEG signal is segmented around event onset. At step 122, artefact rejection is performed, and at step 123, additional transformation (e.g. filtering, curve fitting) required to enhance signal to noise ratio is performed. After single trial waveforms containing extreme values have been identified using absolute or relative thresholds as described above, at step 124, average waveform calculation is performed. Finally, at step 125, feature extraction is performed, wherein features F1, F2, . . . , FN are extracted for each type of observed physiological phenomenon (e.g. ERPs, eye blinks, etc.). Examples of extracted features include but are not limited to: signal shape, amplitude, and latency (relative to stimulus delivery).

Returning to FIG. 4, at step 103, the signal analysis unit 3 compares attributes of the responses (i.e. the extracted features F1, F2, . . . , FN) quantified at step 102 to stored normative values for those attributes in order to designate each of the responses quantified at step 102 as being within or outside of a pre-defined normal range. The normative values, which are also alternatively referred to hereinafter as "reference data", can comprise either baseline values determined to be normative based on research study data or constant values. Example baseline data is shown in Row 3 in FIGS. 6A and 6B and detailed further later herein with respect to those figures, and the use of the constant value 0 as a normative threshold value is also explained with respect to FIGS. 6A and 6B. Specifically, the extracted features are statistically compared to a baseline value or a constant value, wherein the baseline value has been calculated based on data compiled in either of the following manners: by determining the same extracted features for a number of other users of the current biosignal monitoring system 1, or by determining the same features for a sample of random excerpts of the same physiological phenomena (i.e. the same physiological phenomena observed in people not using biosignal monitoring system 1). For example, if one of the responses quantified at step 102 is eye blinks, then step 103 can comprise comparing the peaks in the eye blink signal characteristic determined at step 102 to peaks in available research data for eye blink signal characteristics. Simply put, signal analysis unit 3 determines whether the responses of user U quantified at step 102 fall within a predetermined normal range, the normal range being defined based on the reference data. In choosing signal types to use for fit detection analysis, it will be appreciated that it is preferable to choose signal types for which there are well-defined stereotypical responses. For example, EEG signals provide particularly valuable fit detection analyses, as there are well-documented stereotypical brain responses (such as ERP) to external and internal stimuli that appear in EEG, and there is ample data on spontaneous muscle activity, such as eye blinks or eye movement, that also appear in EEG.

Still referring to step 103, it will be appreciated that there are several statistical tests designed to determine the difference between the mean values of two or more groups (in the present context, the values being compared are the mean values for the data of user U and the mean values for the reference data), and that each statistical test has particular requirements that need to be met in order to be applied to the data. In one non-limiting example, for a t-test or ANOVA (analysis of variance): the tested variables must be continuous (interval/ratio) and approximately normally distributed, the samples must be independent of one another, and the samples must not contain outliers. In another non-limiting example, non-parametric tests, such as a Wilcoxon signed rank test, make no assumptions about the probability distributions of the tested variables but require the data to be paired and to come from the same population and each pair must be chosen randomly and independently. Assuming that necessary requirements are met, the two probability distributions (of the tested variable and the baseline variable, the tested variable being the response of user U quantified at step 102 and the baseline variable being the reference data compiled from a group of subjects) are compared and a probability of rejecting a hypothesis that there is no difference between the two means when that is the case (the null hypothesis) is calculated. This probability, called p-value, is compared to a pre-chosen probability, called significance level (usually $\alpha=0.05$). If the calculated p-value is smaller than the chosen significance level, then the null hypothesis is rejected and we say that there is a difference between the tested value and the baseline. To counteract the increased chance of rejecting the null hypothesis when multiple tests are carried out, the value of a can be reduced proportionally to the number of tests carried out via a procedure known in statistics as Bonferroni correction. Such correction is, however, simply equivalent to selecting another (stricter) significance level.

After the differences between the mean values of the responses of user U and the mean values for the reference data have been determined, the goodness of device fit is then estimated as good (either on a binary or a continuous scale), if the extracted features from the current session show either:

- no significant difference from the baseline, when baseline is built upon good signal quality examples (e.g. no difference with an ERP peak calculated over 10 other users),
- a significant difference from the baseline, when baseline is built upon bad signal quality examples (e.g. ERP peak significantly different from 0),
- that the extracted features are inside of an already predefined range (e.g. ERP peak between 2 and 7 uV), or
- stability of the response with successive tightening or loosening steps, compared to the neighboring values in combination with a predefined threshold or positive comparison to baseline (e.g. if there is no difference in ERP peak between 3 consecutive tightening steps once the ERP peak is above 2 uV, then the middle tightening step is selected as optimal), or if the response is classified as being the expected physiological response by a machine learning model 30 that can be optionally included in signal analysis unit 3 (as shown in FIG. 2). Machine learning model 30 can be implemented as, for example and without limitation, a deep neural network or a support vector machine. Regardless of the particular implementation of machine learning executed by machine learning model 30, it will be appreciated that machine learning model 30 is trained using the aforementioned reference data to identify the relevant features of the user response (defined at step 102) that are most useful for discriminating between an expected response and a weak response, as well as for discriminating between an expected response and a lack of response.

Whether monitoring system 1 includes bio event detector 11 or signal actuator 11', if method 100 is executed prior to the upcoming session of biomonitoring device 2 use and if signal analysis unit 3 determines that the user response is within the normal range after performing step 103, process 100 proceeds to step 105 where process 100 is deemed complete and user interface 4 indicates to user P that the device is deemed to be properly fit and positioned for the upcoming monitoring session. If, however, signal analysis unit 3 determines after performing step 103 that the user U data is outside of the normal range, process 100 proceeds to step 104 wherein a notification is delivered to user U via user interface 4 to inform user U that the fit and/or positioning of biomonitoring device 2 needs to be adjusted. Notifications provided to user U at steps 104 and 105 can include, for example and without limitation, a written notification displayed on a screen of the user interface 4, a light included on the biomonitoring device 2 illuminating green at step 105 to indicate good fit while instead illuminating red at step 104 to indicate poor fit, or a "happy" tone being played at step 105 to indicate good device fit.

Continuing to refer to step 104, in some exemplary embodiments, user interface 4 provides specific recommendations or instructions to user U for adjusting the fit and/or positioning of the biomonitoring device 2. For example and without limitation, user interface 4 may comprise a mobile app with clear instructions that are narrated and/or pictured for user U. In the case of sleep headband 2, such instructions provided to user U may pertain to tightening the fit adjuster 10, or sliding sleep headband 2 in order to adjust the placement of forehead band 21 and scalp band 22 relative to the head of user U. Specifically, user U may be directly instructed to slide sleep headband 2 slightly up or down in order to avoid trapping hair between the bio sensors 5 and the skin, or to slide sleep headband 2 slightly left or right in order to avoid contact between the bio sensors 5 and the temples. In another non-limiting example where biomonitoring device 2 comprises an adhesive patch such as the ones used for EKG monitoring, the recommendations or instructions provided to user U at step 104 can include directing user U to move the patch to a different location on the body in order to improve the quality of the signal sensed by the patch.

Continuing to refer to step 104, in additional exemplary embodiments, biomonitoring device 2 can comprise predefined fit adjustment markers, and user U can be guided through a calibration procedure. In an illustrative example using sleep headband 2, such a calibration procedure can comprise instructing user U to tightly fasten the fit adjuster 10 and subsequently loosen fit adjuster 10 incrementally in steps according to the predefined markers. In other exemplary embodiments, user interface 4 can be implemented at least partially directly on biomonitoring device 2 as a number of sound, vibration, or visual indicators. For example and without limitation, a light can be included on biomonitoring device 2 that illuminates red if the bio signals sensed during device setup are unsatisfactory and illuminates green if the bio signals sensed during device are satisfactory, or a speaker can emit a "happy" sound or vibration if the device setup is deemed to be satisfactory.

Furthermore, other exemplary embodiments of method 100 can include a step 104A, in which user U can provide additional feedback about the user's perceived comfort to controller 8 through user interface 4, or controller 8 itself may provide additional non-biosignal related feedback, and wherein such additional feedback is also used (in addition to the biosignal data) by signal analysis unit 3 to form fit/positioning adjustment recommendations for user U at step 104. Non-limiting examples of the additional non-bio signal feedback that can be provided by controller 8 include the attributes previously enumerated with respect to signal quality parameter module 12 shown in FIG. 2: impedance, signal power, noise, and signal-to-noise ratio (SNR).

Figure 6A:
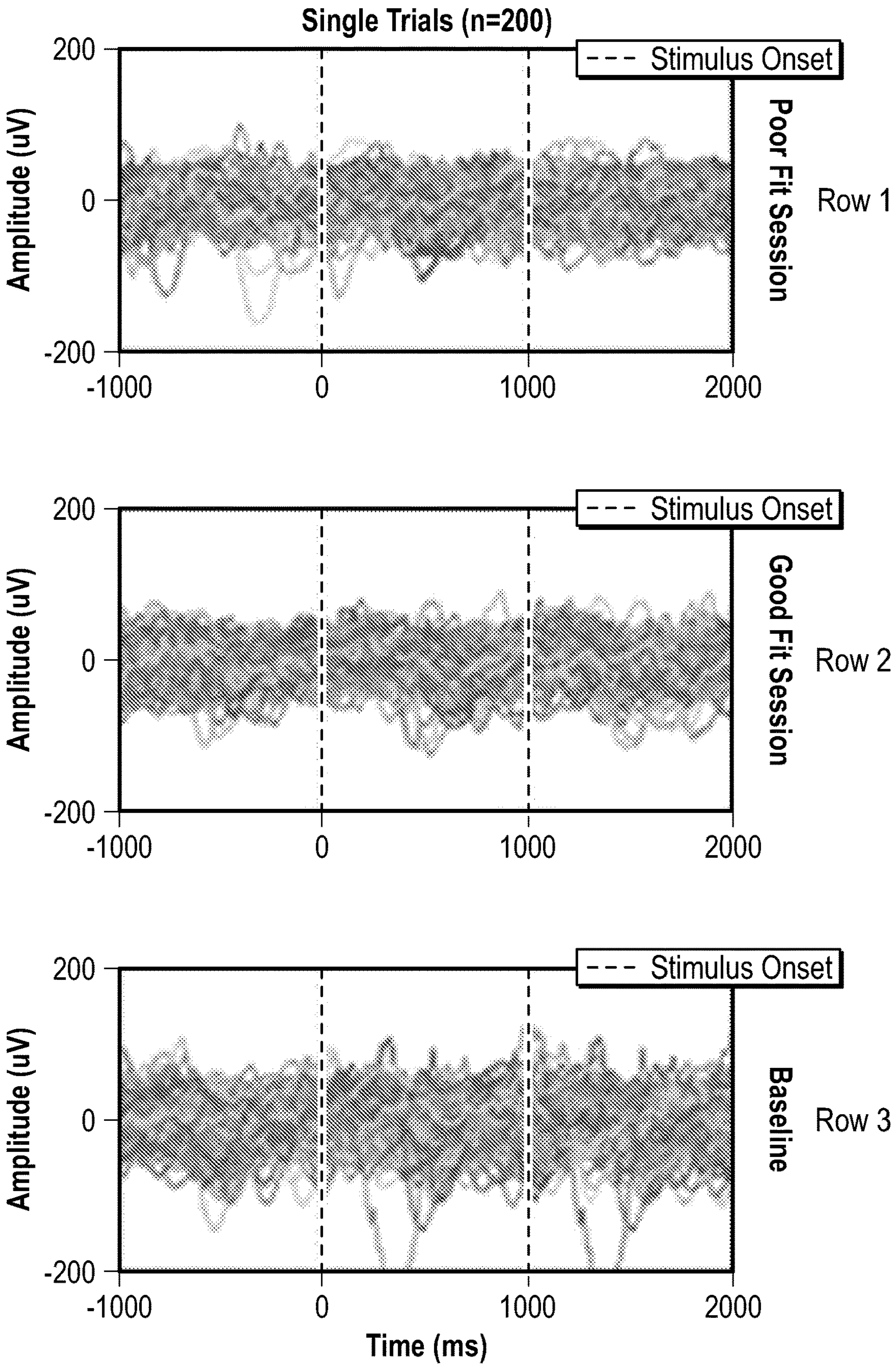
FIG. 6A shows two graphs displaying several individual EEG signals corresponding to different fit conditions of the biomonitoring device shown in FIG. 1A while a wearer is using the device, as well as a graph of reference data used as a baseline for determining whether EEG signals sensed while a user is wearing the biomonitoring device denote a good fit or a poor fit, according to an exemplary embodiment of the disclosed concept.
Figure 6B:
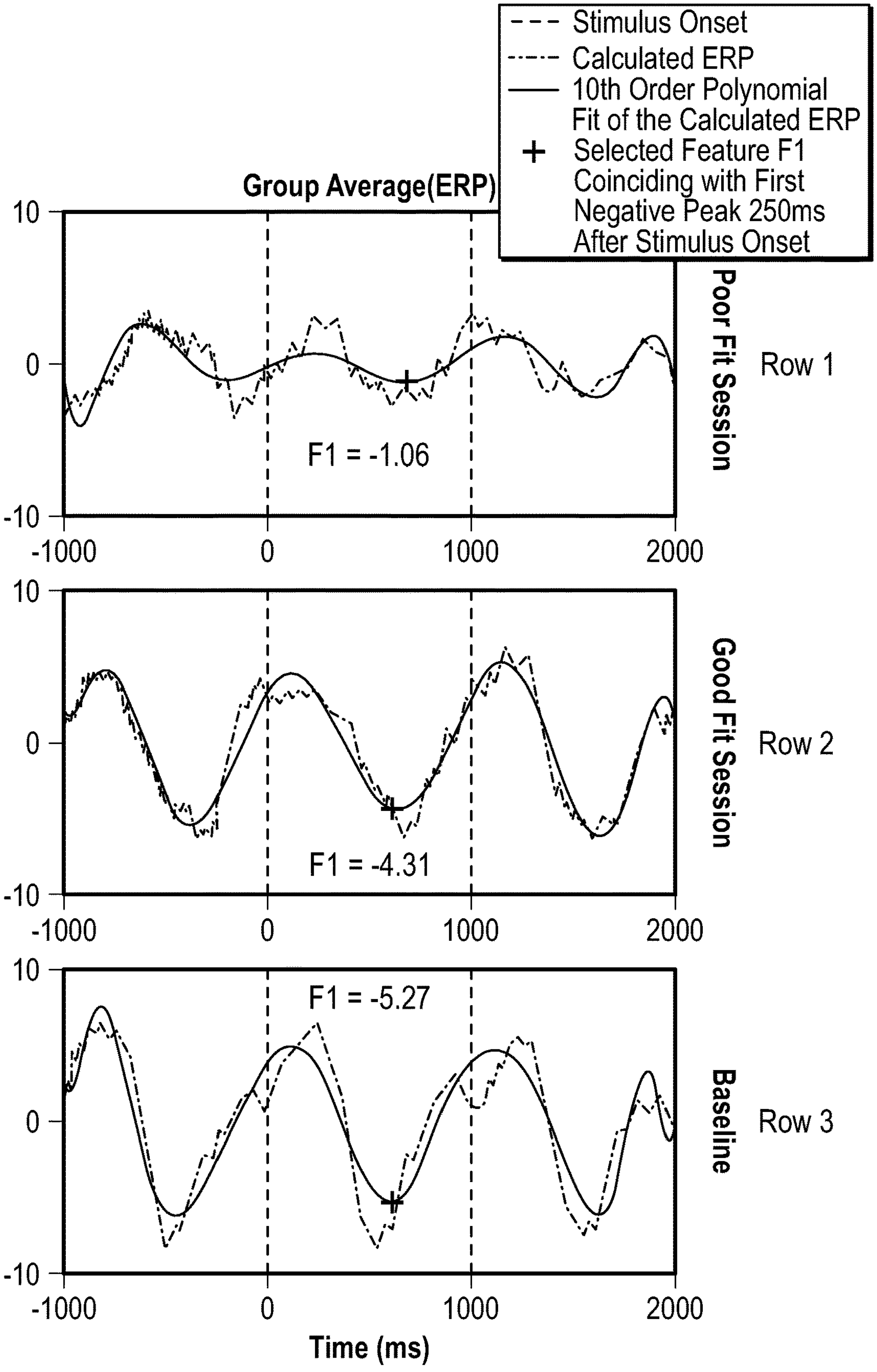
FIG. 6B shows graphs displaying group average event related potential (ERP) values calculated from the EEG signals shown in FIG. 6A, representative of reference data used by the biosignal monitoring system in order to determine whether device fit and positioning is satisfactory, according to an exemplary embodiment of the disclosed concept.

Referring now to FIGS. 6A and 6B in addition to FIG. 4, an illustrative example of method 100, and steps 102 and 103 in particular, is provided. The graphs in FIG. 6A display waveforms produced based on actual scalp EEG data from test study subject users of sleep headband 2. As indicated by the annotations in FIGS. 6A and 6B, the Row 1 graphs ("Poor Fit Session") display data sensed by bio sensors 5 when sleep headband 2 was poorly-fitted for the user and not expected to accurately measure EEG of the user, the Row 2 graphs ("Good Fit Session") display data sensed by bio sensors 5 when sleep headband 2 was well-fitted for the user and expected to accurately measure EEG of the user, and the Row 3 graphs ("Baseline") display the normative data referred to above, comprising signals sensed by EEG sensors properly placed on a group of research subjects similarly to how scalp sensors 52 would be placed on a sleep headband 2 user. The three graphs in FIG. 6A display individual waveform data measured by EEG sensors for 200 different signal detection events, and the three graphs in FIG. 6B display waveforms representing the average of the 200 waveforms (i.e. the ERP) calculated for the EEG data shown in FIG. 6A.

Continuing to refer to FIGS. 6A and 6B, as indicated by the "stimulus onset" lines in FIG. 6A, a number of beeps (auditory stimulation tones) were played during device set up. Three-second long segments around tone onset (starting 1 second before and ending 2 seconds after stimulus onset) were extracted from the pre-processed EEG signal. For the group of tones played (n=200), the time locked average (i.e. ERP) was calculated and fit to a polynomial of order 10. Then, the first negative peak after 250 ms from tone onset (feature F1) was detected. The value of F1 is the mean EEG amplitude at that point. So, in order to test the difference between the mean of each tone group (the Poor Fit Session comprising one tone group and the Good Fit Session comprising another tone group) and the Baseline (the normative value), the distributions of amplitudes at the time when feature F1 occurs was calculated for each trial in both tone groups and compared. The amplitude values were normally distributed and a t-test was applied to determine if the means of the Poor Fit Session values and the Baseline values were statistically different, and if the means of the Good Fit Session values and the Baseline values were statistically different. As expected, the result of the t-test between the Poor Fit Session value and the Baseline value (the normative value) was found to be significant and hence, indicate that the device needed adjustment. Also as expected, the test between the Good Fit Session value and the Baseline (the normative value) was found to be not significant and hence, indicate that the device needed no further adjustments.

Still referring to FIGS. 6A and 6B, alternative methods for executing steps 102 and 103 can be used. A first alternative method compares the inherent statistical significance of the calculated F1 feature to the value 0, instead of comparing features of the Good Fit session data and Poor Fit session data to the Baseline data. For example, the calculated F1 peak for the Poor Fit session is non-significant in comparison to 0, and the calculated F1 peak for the Good Fit session is significant in comparison to 0. Accordingly, for a user of system 1, if the signal analysis unit calculates the same feature F1 as calculated for the data used in FIGS. 6A and 6B, then a non-significance relative to 0 would indicate bad fit/positioning of sleep headband 2 (i.e. fit and/or positioning adjustment needed), while a significance relative to 0 would indicate good fit/positioning (i.e. no adjustments to sleep headband 2 needed). In a second alternative method, the size of the physiological peak can be further used to give a more continuous estimate, e.g. F1=2 denotes an adequate fit, F1=3 denotes a good fit, and F1>4 denotes a very good fit. In addition, there are several alternatives to using the first negative peak after 250 ms as the extracted feature for comparison, non-limiting examples of which include: the amplitude of the first positive peak in the first 250 ms, the mean amplitude in a window of 100 ms surrounding either the positive or negative peaks, and the area under the curve in the 250 ms around a peak.

The methods and systems disclosed herein offer an important advantage over simple signal quality measures such as impedance, noise power, signal-to-noise ratio (SNR), and others by evaluating the quality of the meaningful physiological responses of the body sensed by a biosignal monitoring device, wherein said physiological responses are used during execution of the primary function of the device, prior to the device being used for its primary purpose. Stereotypical brain responses to an external or internal stimuli, such as ERP, or muscle activity, such as eye blinks or eye movement, are very convenient markers, and the systems and methods disclosed herein advantageously utilize the fact that the shape and amplitude of these EEG phenomena are well studied and can be easily modeled for a particular biosignal monitoring system.

Another related advantage offered by the methods and systems disclosed herein is providing, for those biomonitoring systems 1 that include actuators 6, a combined estimate of both sensor 5 and actuator 6 placement, as having an estimate of only sensor 5 placement or only actuator 6 placement may not provide an accurate depiction of whether the overall monitoring system will function properly. For example, as previously stated, a dry electrode that is just touching the skin can have a very low noise level, but the lack of pressure will cause the dynamic range of the signal to be low. In another example, a SNR defined over two ranges that fluctuate in the same direction in case of a bad signal can incorrectly suggest that the quality of device fit is high when it is in fact low. Furthermore, an actuator 6 (e.g. for sleep headband 2, a bone conduction speaker used to deliver deep sleep enhancing auditory tones) that does not make proper contact will not affect the sensors' impedance at all but will not deliver the anticipated effect. The current invention looks at the meaningful system-operation-relevant physiological phenomena and judges the placement of both sensors 5 and actuators 6, and ensures the proper functioning of a complete biosignal monitoring system by guiding a user to make any necessary adjustments to the fit and placement of said sensors and actuators prior to using the monitoring system.

As previously stated with respect to FIG. 1A and throughout the present disclosure, biosignal monitoring devices 2 other than sleep headband 2 to which the disclosed methods and systems are applicable include, but are not limited to, wrist-worn devices, respiration belts, smart adhesive patches, and finger sensors. In a first non-limiting example, in wrist-worn devices that measure heart rate variability (HRV) using PPG, the PPG signal is produced when LED actuators emit light, which is reflected by the skin and picked up by photo diodes. The amplitude of the response will vary depending on how well the LED and diodes are placed on the skin. Response attributes such as the shape, amplitude, and possibly latency of the response in a user can be compared with a normative value(s) identified beforehand, similarly to EEG and ERP signals previously discussed herein. If the response attribute values are out of range, the signal analysis unit 3 can provide the user with feedback that the band needs to be tightened.

In another non-limiting example, in a smart adhesive patch with biosensors, the methods disclosed herein can be used to ensure placement of the patch on the correct body area, or to ensure that the sensor has been correctly adhered to the skin (for instance, when proper functioning of the patch necessitates blocking all ambient light with the adhesive area), and the user can be instructed to press the adhesive to the skin more firmly if necessary. In a further non-limiting example, in an application where device fit is expected to dynamically change over the usage of a device, a measured ERP response can also be used to judge if currently measured signals should be used. E.g. in PPG applications, measuring average heart rate can be done reliably under bad device wearing conditions and/or while a user is in motion, while detection of individual heart beats require proper device fit, among other conditions.

In the claims, any reference signs placed between parentheses shall not be construed as limiting the claim. The word "comprising" or "including" does not omit the presence of elements or steps other than those listed in a claim. In a device claim enumerating several means, several of these means may be embodied by one and the same item of hardware. The word "a" or "an" preceding an element does not omit the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A fit and positioning optimization system for a biosignal monitoring device, the biosignal monitoring device being configured to monitor physiological signals of a user, the biosignal monitoring device having a number of bio sensors configured to sense physiological activity of the user, the optimization system comprising:

a fit event detector comprising
   a number of sensory event actuators configured to deliver sensory stimuli to the user to stimulate the physiological signals of the user; and a controller comprising a signal analysis unit and configured to be in electrical communication with the number of bio sensors and the fit event detector;

wherein the number of sensory event actuators are configured to transmit information about a timing of delivered sensory stimuli to the signal analysis unit;

wherein the signal analysis unit is configured to determine a trigger time of at least one physiological signal produced in the user in response to the sensory stimuli;

wherein the controller is configured to use the fit event detector to define a user response in response to the sensory stimuli based on physiological activity signals sensed by the number of bio sensors, wherein the signal analysis unit is configured to store physiological response reference data and to determine if the user response is within a predefined normative range based on the reference data, wherein the controller is configured to form a recommendation, based on whether the user response is within the normative range, indicating whether adjustments to the fit or positioning of the biosignal monitoring device are required in order to optimize monitoring of the physiological signals, and wherein the controller is configured to alert the user of the recommendation through a user interface.

2. The optimization system of claim 1, wherein the number of sensory event actuators are configured to deliver multiple types of sensory stimuli to the user;

wherein the physiological activity signals sensed by the bio sensors are based on the multiple types of sensor stimuli; and wherein the user response is defined as an average response over all stimulated events.

3. The optimization system of claim 1, wherein the number of sensory event actuators are configured to deliver multiple types of sensory stimuli to the user;

wherein the physiological activity signals sensed by the bio sensors are based on the multiple types of sensor stimuli, and wherein the user response is defined as an average response based on a timing of the delivery of the sensory stimuli during set up of the device.

4. The optimization system of claim 1, wherein the number of bio sensors comprises a number of electroencephalogram (EEG) sensors, wherein the signal analysis unit is configured to calculate event relate potentials (ERPs) for physiological activity sensed by the EEG sensors.

5. The optimization system of claim 4, wherein the signal analysis unit is configured to:

determine a time at which the user response was triggered, choose a pre-determined interval of time surrounding onset of a single physiological fit event of the sensed physiological activity;

calculate ERP values elicited in the user by the single physiological fit event and produce an ERP waveform with the ERP values;

identify, as a feature F1, one of: a first negative ERP peak occurring after a first predetermined amount of time after onset of the single physiological fit event; a first positive ERP peak occurring within the first predetermined amount of time after the onset of the single physiological fit event; a mean ERP amplitude occurring within a first predetermined window of time surrounding either of positive or negative ERP peaks; or an area under a curve in a second predetermined window around a given ERP peak, produce a probability distribution of the ERP values at a time F1 occurs;

apply a statistical test to determine if there is a statistically significant difference between a time F1 value elicited in the user and a corresponding ERP value in the reference data corresponding to the predetermined amount of time after the onset of the single physiological fit event; and make a determination that the biosignal monitoring device needs fit or positioning adjustments if there is a statistically significant difference between the time F1 value and the corresponding ERP value in the reference data, or make a determination that the biosignal monitoring device does not need fit or positioning adjustments if there is no statistically significant difference between the time F1 value and the corresponding ERP value in the reference data.

6. The optimization system of claim 4, wherein the signal analysis unit is configured to:

determine a time at which the user response was triggered;

choose a pre-determined interval of time surrounding onset of a single physiological fit event of the sensed physiological activity;

calculate ERP values elicited in the user by onset of the single physiological fit event and produce an ERP waveform with the ERP values;

curve fit the ERP waveform;

identify a first negative peak as a value F1 occurring a predetermined amount of time after the onset of the single physiological fit event;

produce a normal distribution of the ERP values at a time F1 occurs;

determine if there is a statistically significant difference between the F1 value elicited in the user and the value 0; and make a determination that the biosignal monitoring device needs fit or positioning adjustments if there is not a statistically significant difference between the F1 value and the value 0, or make a determination that the biosignal monitoring device does not need fit or positioning adjustments if there is a statistically significant difference between the F1 value and the value 0.

7. A biosignal monitoring device comprising the fit and positioning optimization system of claim 1, wherein the biosignal monitoring device is configured to monitor physiological signals of the user based on physiological activity of the user sensed by the number of bio sensors.

8. The biosignal monitoring device of claim 7, wherein the biosignal monitoring device is a wearable sleep therapy device, wherein the number of bio sensors comprise a number of EEG sensors configured to sense physiological activity of the user;

wherein the wearable sleep therapy device is configured to monitor sleep stages of the user based on the physiological activity sensed by the number of EEG sensors;

wherein the number of sensory event actuators comprises a number of speakers configured to selectively deliver auditory tones to the user;

wherein the signal analysis unit is configured to use the fit event detector to define the user response in response to the auditory tones based on physiological activity signals sensed by the number of EEG sensors.

9. The biosignal monitoring device of claim 8, wherein the wearable sleep therapy device is a sleep headband.

10. A method for optimizing fit and positioning for a biosignal monitoring device, the biosignal monitoring device being configured to monitor physiological activity of a user, the biosignal monitoring device comprising:

a number of bio sensors;

a fit event detector comprising a number of sensory event actuators configured to deliver sensory stimuli to the user to stimulate the physiological activity of the user;

a controller configured to be in electrical communication with the number of bio sensors and the fit detector and comprising a signal analysis unit, the signal analysis unit being configured to store physiological response reference data;

the method comprising delivering with the number of sensory event actuators sensory stimuli to the user;

transmitting with the number of sensory event actuators information about a timing of delivered sensory stimuli to the signal analysis unit;

sensing physiological activity of the user with the number of bio sensors;

determining with the signal analysis unit a trigger time of at least one physiological signal produced in the user in response to the sensory stimuli, defining, using the fit event detector, a user response in response to the sensory stimuli based on the sensed physiological activity;

determining, with the signal analysis unit, if the defined user response is within a predefined normative range based on the reference data;

forming a recommendation, with the signal analysis unit, indicating whether the fit or positioning of the device require adjustments in order to optimize monitoring of physiological activity, based on whether the defined user response is within the normative range; and alerting the user of the recommendation through a user interface.

11. The method of claim 10, further comprising:

delivering, with the sensory event actuator, multiple types of sensory stimuli to the user;

defining the user response in response to the multiple types of sensory stimuli, based on the sensed physiological activity sensed by the number of sensors; and averaging the user response over all stimulated events.

12. The method of claim 10, wherein the device comprises the number of sensory event actuators and the method further comprises:

initiating, with the number of sensory event actuators, delivery of physiological stimuli to the user at predetermined intervals during set up of the device; and defining the user response with the signal analysis unit during set up of the device, based on a timing of the delivery of the physiological stimuli.

13. The method of claim 10, wherein the number of bio sensors comprises a number of electroencephalogram (EEG) sensors, and wherein the method further comprises calculating with the signal analysis unit event related potentials (ERPs) for physiological activity sensed by the EEG sensors.

14. The method of claim 13, further comprising:

determining, with the signal analysis unit, a time at which the user response was triggered;

choosing, with the signal analysis unit, a pre-determined interval of time surrounding onset of a single physiological fit event;

calculating, with the signal analysis unit, ERP values elicited in the user by the onset of the single physiological fit event and producing an ERP waveform with the ERP values;

identifying with the signal analysis unit, as a value F1, one of: a first negative ERP peak occurring after a first predetermined amount of time after onset of a stimulus event; a first positive ERP peak occurring within the first predetermined amount of time after the onset of the stimulus event; a mean ERP amplitude occurring within a first predetermined window of time surrounding either of positive or negative ERP peaks; or an area under a curve in a second predetermined window around a given ERP peak;

producing, with the signal analysis unit, a probability distribution of the ERP values at the time F1 occurs;

applying, with the signal analysis unit, a statistical test to determine if there is a statistically significant difference between the F1 values elicited in the user and corresponding ERP values in the reference data corresponding to the predetermined amount of time after stimulus event onset; and forming a recommendation with the signal analysis unit that the biosignal monitoring device needs fit or positioning adjustments if there is a statistically significant difference between the F1 value and the corresponding ERP value in the reference data, or forming a recommendation with the signal analysis unit that the biosignal monitoring device does not need fit or positioning adjustments if there is no statistically significant difference between the F1 value and the corresponding ERP value in the reference data.

15. The method of claim 13, further comprising:

determining, with the signal analysis unit, a time at which the user response was triggered;

choosing, with the signal analysis unit, a pre-determined interval of time surrounding delivery of a single physiological stimulus event onset;

calculating, with the signal analysis unit, ERP values elicited in the user by the stimulus event onset and producing an ERP waveform with the ERP values;

identifying, with the signal analysis unit, a first negative peak as a value F1 occurring a predetermined amount of time after the stimulus event onset;

producing, with the signal analysis unit, a normal distribution of the ERP values at the time F1 occurs;

determining, with the signal analysis unit, if there is a statistically significant difference between the F1 value elicited in the user and the value 0; and forming a recommendation with the signal analysis unit that the biosignal monitoring device needs fit or positioning adjustments if there is not a statistically significant difference between the F1 value and the value 0, or forming a recommendation with the signal analysis unit that the biosignal monitoring device does not need fit or positioning adjustments if there is a statistically significant difference between the F1 value and the value 0.

* * * * *